(12) United States Patent
Ahmed et al.

(10) Patent No.: US 10,292,709 B1
(45) Date of Patent: May 21, 2019

(54) DEVICE FOR SUTURELESS REPAIR OF AN INJURED NERVE

(71) Applicant: KING SAUD UNIVERSITY, Riyadh (SA)

(72) Inventors: Durria Ahmed Abdulmaged Ahmed, Riyadh (SA); Ghada Abdulrahman Alnafisa, Riyadh (SA); Mohammad Manna Al-Qattan, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/189,905

(22) Filed: Nov. 13, 2018

(51) Int. Cl.
| | |
|---|---|
| *A61B 18/18* | (2006.01) |
| *A61B 17/11* | (2006.01) |
| *A61B 17/02* | (2006.01) |
| *A61B 17/10* | (2006.01) |
| *A61M 1/00* | (2006.01) |
| *A61B 17/00* | (2006.01) |

(52) U.S. Cl.
CPC ...... *A61B 17/1128* (2013.01); *A61B 17/0218* (2013.01); *A61B 17/02* (2013.01); *A61B 17/10* (2013.01); *A61B 2017/00902* (2013.01); *A61B 2017/0225* (2013.01); *A61L 2430/32* (2013.01); *A61M 1/008* (2013.01); *A61M 1/0066* (2013.01)

(58) Field of Classification Search
CPC ..... A61B 17/02; A61B 17/0218; A61B 17/10; A61B 17/11; A61B 17/1107; A61B 17/1114; A61B 17/1128; A61B 17/1132; A61B 17/1146; A61B 2017/00902; A61B 2017/0225; A61L 2430/32; A61M 1/0058; A61M 1/0066; A61M 1/008; A61M 1/0084; A61M 1/0088
See application file for complete search history.

(56) References Cited

U.S. PATENT DOCUMENTS

| | | | |
|---|---|---|---|
| 5,307,709 A | 5/1994 | Byrne | |
| 5,486,172 A * | 1/1996 | Chess | A61B 18/203 206/524.4 |
| 5,776,106 A * | 7/1998 | Matyas | A61M 25/02 128/DIG. 26 |
| 8,114,018 B2 | 2/2012 | Park et al. | |
| 8,449,562 B2 * | 5/2013 | Swain | A61B 17/11 606/152 |
| 9,408,956 B2 * | 8/2016 | Zamierowski | A61M 1/0084 |
| 9,414,827 B2 | 8/2016 | Solomon | |
| 2002/0095150 A1 * | 7/2002 | Goble | A61B 17/3423 606/41 |

(Continued)

*Primary Examiner* — Todd J Scherbel
(74) *Attorney, Agent, or Firm* — Richard C. Litman

(57) ABSTRACT

The device for sutureless repair of an injured (severed) nerve includes a securement band connected by a transparent membrane to form a loop. The band includes two opposing approximation claws that extend into the region of the transparent membrane. An aperture in the transparent membrane is covered by an enclosure having an inlet nozzle and an outlet nozzle. An elongate member having a blade on its bottom end extends through an aperture in the top of the enclosure. The band is strapped around the patient's limb with the transparent membrane adhesively secured over the incision, the severed nerve ends are irrigated with saline and air is evacuated in the process. The blade incises the severed ends of the nerve to expose fresh nerve tissue under vacuum, and the severed ends are approximated. The device is left in place for the severed nerve ends to reunite.

15 Claims, 4 Drawing Sheets

(56) References Cited

U.S. PATENT DOCUMENTS

2006/0235279 A1   10/2006  Hawkes et al.
2007/0066945 A1*  3/2007  Martin ................ A61M 1/0058
                                                             604/313
2012/0296369 A1*  11/2012  Atthoff ............. A61B 17/1322
                                                             606/202

* cited by examiner

DEVICE FOR SUTURELESS REPAIR OF AN INJURED NERVE

BACKGROUND

1. Field

The disclosure of the present patent application relates to peripheral nerve repair, and particularly to a device for sutureless repair of an injured nerve.

2. Description of the Related Art

Nerve injuries without a defect or with a short gap are usually treated by end-to-end coaptation. The normal nerve segments proximal and distal to the site of neurorrhaphy (joining together of two parts of a divided nerve, usually by suturing) are sufficiently extensible to compensate for the short defects. If there is a longer defect, a neurorrhaphy without tension at the site of the repair cannot be performed and surgical repair of nerve gaps greater than 20 mm is commonly achieved by autologous nerve grafts. An autologous nerve graft provides Schwann cells (SC), growth factors and basal lamina components, and is the current gold standard, but has associated problems. Scarring, neuroma formation, and poor sensory function recovery are common consequences. Previous studies have reported a poor recovery of sensation, as well as only partially recovered motor function in most cases. Autologous alternatives have been sought and include autologous conduits, such as venous or arterial conduit grafts, but these did not show any functional benefits compared with standard nerve grafts. Peripheral nerve allografts using cadaver tissue have been tested, but they have many limitations, especially because of the undesirable long-term immunosuppressive therapy required.

In order to achieve a better clinical outcome, several synthetic nerve repair conduits have been studied to replace nerve autografts and allografts. Non-degradable materials, such as silicone, polytetrafluorethylene (PTFE) and polypyrrole (PPY), have been thought to provide a permissive environment for outgrowing axons, allowing the supportive supply of neurotrophic factors and SC. However, it was noted that compression syndromes often occurred because of their non-degradable nature and their inability to adapt to the nerve growth and maturation. Moreover, increased scarring and irritation of the patient has been described. Increasingly, synthetic nerve repair conduits used for bridging neural gaps are made of biodegradable or bioresorbable materials. Among these, poly 3-hydroxybutyrate (PHB) nerve repair conduits have gained particular interest and have been extensively investigated. PHB nerve repair conduits have a soft malleable consistency, good tensile strength and flexibility. PHB nerve repair conduits show early vascularization after implantation and are resorbed over a period of two years. These above-mentioned nerve repair conduits have a rather long resorption time, whereas an optimal nerve repair conduit should dissolve within weeks to a few months, having supported the regenerating axons to cross the nerve gap and allowing neurotrophic factors to penetrate during the early phase of regeneration.

Thus, a device for sutureless repair of an injured nerve solving the aforementioned problems is desired.

SUMMARY

The device for sutureless repair of an injured (severed) nerve includes a strap or securement band connected by a transparent membrane to form a loop. The securement band includes two opposing approximation claws that extend into the region of the transparent membrane. An aperture in the transparent membrane is covered by an enclosure having an inlet nozzle and an outlet nozzle. An elongate member having a blade on its bottom end extends through an aperture in the top of the enclosure. The elongate member has the ability to translate along its length, rotate, and pivot with respect to the enclosure.

A method of sutureless repair of an injured nerve includes sealing the transparent membrane around the nerve repair site and irrigating the site, using the nozzles on the enclosure. The dead ends of the severed nerve are then cut off using the blade. The severed nerve ends are then approximated and the transparent membrane is collapsed around the ends so that they are contained in an air-free, physiological healing environment.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
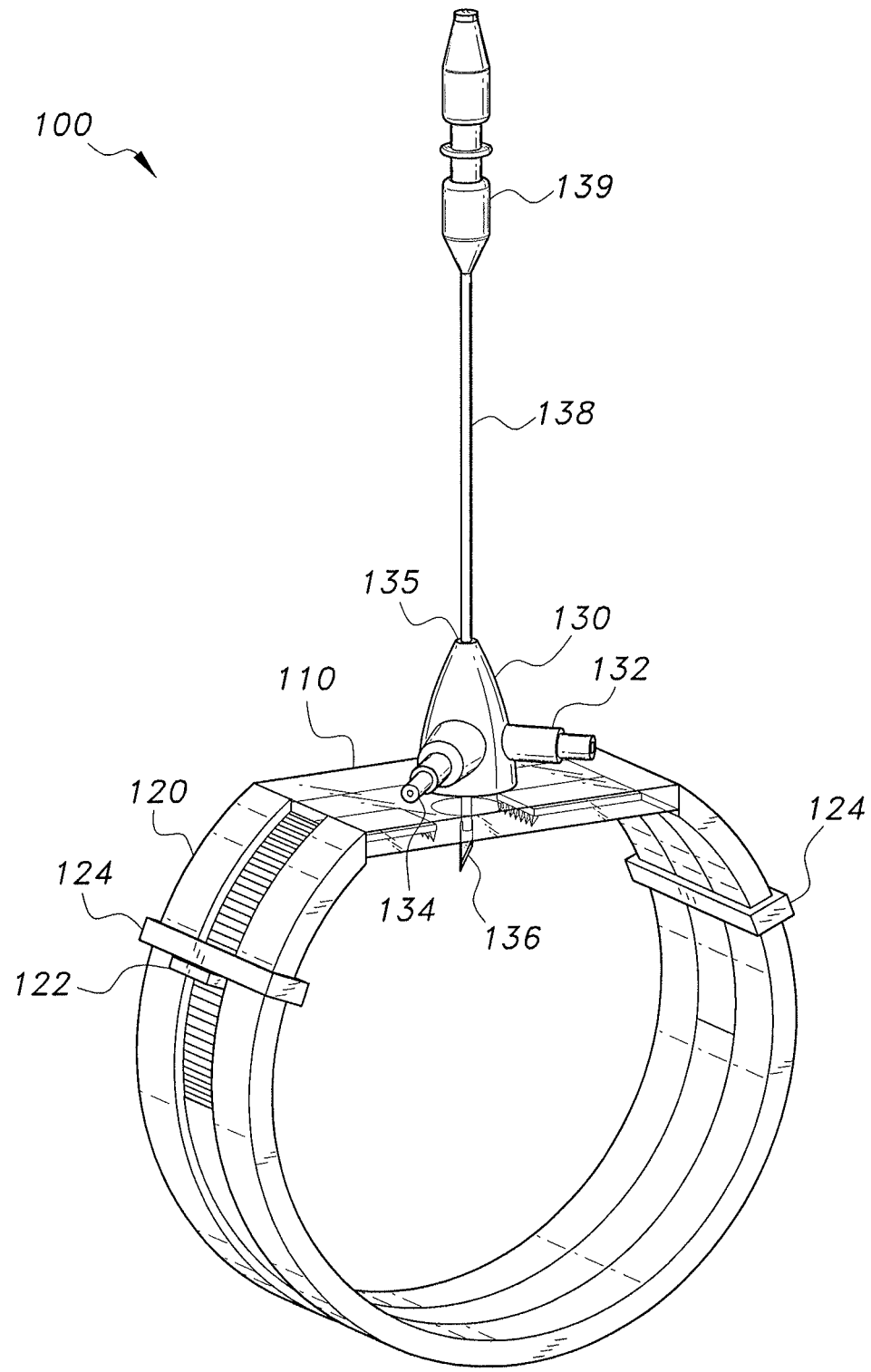
FIG. 1 is a perspective view of the device for sutureless repair of an injured nerve.
Figure 2:
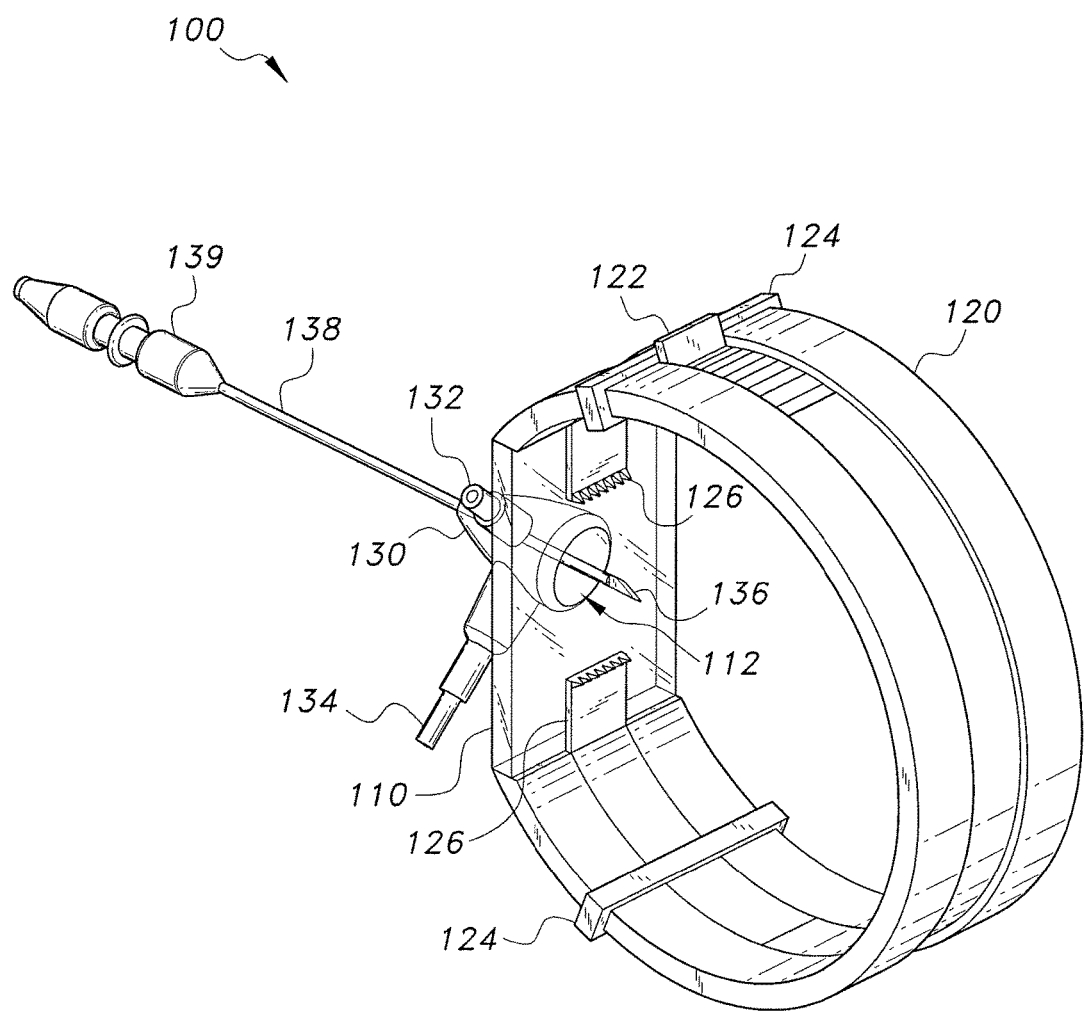
FIG. 2 is a perspective view of the device for sutureless repair of an injured nerve as seen from below the transparent membrane.

As shown in FIGS. 1 and 2, the device 100 for sutureless repair of an injured nerve includes a securement band 120 connected by a transparent membrane 110 to form a loop. The band 120 includes two opposing approximation claws 126 that extend into the region of the transparent membrane 110. An aperture 112 in the transparent membrane 110 is covered by an enclosure 130 having an inlet nozzle 132 and an outlet nozzle 134. An elongate member 138 having a blade 136 on its bottom end extends through an aperture 135 in the top of the enclosure 130. The elongate member 138 has the ability to translate along its length, rotate, and pivot with respect to the enclosure 130.

The device 100 is held in place by a band 120, which is designed to wrap around a patient's limb. Typically, peripheral nerve trauma will occur to one of a person's appendages, and the band 120 will be dimensioned according to the appendage it is intended to wrap around. For example, a device 100 for use on a patient's leg will have a larger diameter band 120 than a device 100 for use on a patient's arm or finger. The band 120 may have adjustable or elastic properties to allow for a secure fit on appendages of different size or configuration. For example, the band 120 may have a mechanism that adjustable, similar to a watchband (watchstrap), or opposing sides of the band 120 may have hook and loop fasteners. The opposing ends of the band 120 are connected to opposing sides of the transparent membrane 110, thereby holding the membrane in place against the patient's skin when the band 120 is wrapped around the patient.

The transparent membrane 110 is designed to completely cover an incision that exposes the severed nerve ends. An air- and liquid-tight barrier between the incision and the outside environment is formed by the transparent membrane 110. This barrier prevents oxygen, pathogens, and debris from entering the surgical site, while retaining moisture and fluids in the surgical site. In addition, the barrier also allows for a negative pressure to be maintained in the surgical site after the approximation procedure. The transparency of the membrane 110 allows a surgeon to view the incision and nerves under the membrane 110 for conducting the procedure. An adhesive or an adhesive-like coating is applied to the lower/skin-contacting surface of the transparent membrane 110 to create the air- and liquid-tight seal between the transparent membrane 110 and adjacent skin.

Approximation claws 126 extend out from the band 120 towards the aperture 112 in the transparent membrane 110. The approximation claws 126 are designed to approximate the nerve ends by pulling on the skin adjacent the nerve ends. In this embodiment, the approximation claws 126 are shown as a planar members having sharp protrusion extending down from their terminal ends. The approximation claws 126 are connected to adjustors 122, which allow a practitioner to adjust the approximation of the nerve by moving the adjustors 122. For example, the practitioner may push down on the adjustors 122, which will approximate the nerve ends. Alternatively, the approximation claws 126 may act to open the incision so the practitioner may view the area inside the incision.

The adjustors 122 slide within a track on the band 120. Once the nerve ends are properly approximated, by the practitioner moving the adjusters 122, the adjustors 122 can be locked in place by keeper loops 124 that maintain the adjuster's 122 positions relative to the band 120.

The enclosure 130 surrounds the aperture 112 in the transparent membrane 110 with an air- and liquid-tight seal between the enclosure 130 and the transparent membrane 110. The enclosure 130 tapers in as it extends away from the membrane 110 resulting in a small diameter hole 135 for accepting the elongate member 138 attached to the blade 136. An inlet nozzle 132 and an outlet nozzle 134 extend out from the enclosure's wall. The nozzles 132,134 are designed for providing irrigation to the surgical area through flowing saline solution into the inlet nozzle 132 and subsequently draining the solution and debris from the surgical site through the outlet nozzle 134. One-way valves may be incorporated into the nozzles 132,134 to prevent retrograde flow. The inlet nozzle 132 and outlet nozzle 134 may also have shut-off valves to close the nozzles 132,134 when not in use. The nozzles 132,134 may be dimensioned and configured to directly accept polymer tubing or known quick release adapters. The outlet nozzle 134 may be located on an upper portion of the enclosure 130 to assist in purging all of the air from the sealed area.

The elongate member 138 having the blade 136 at its bottom end extends through an aperture 135 at the top of the enclosure 130. The elongate member 138 has the ability to translate along its length, rotate, and pivot with respect to the enclosure 130. This movement allows the practitioner to cut the nerve ends by moving a handle 139 at the top of elongate member 138. A tight fit is maintained between the elongate member 138 and the hole 135 through which it extends to maintain the air- and liquid-tight seal. A sealing structure or O-ring may also be used to assist in sealing the opening 135. The enclosure 130 may include a blade lock, which locks the blade 126 in place when it is not being used, thus preventing unintended trauma in the surgical site after the nerve ends have been cut. The blade lock may be a pressure fit groove or an insertion slot. In addition, the elongate member 138 may have a break-away portion that allows the majority of the elongate member 138 and handle 139 to be removed once the blade 136 is no longer necessary and is fully locked in the blade lock.

FIG. 2 shows the bottom surface of the transparent membrane 110. As previously discussed, the elongate member 138 and attached blade 136 extend through an aperture in the membrane 110. The aperture 112 is covered by the enclosure 130, containing an inlet nozzle 132 and an outlet nozzle 134. The approximation claws 126 extend out from the ends of the band 120 and along the lower surface of the transparent membrane 110.

Figure 3:
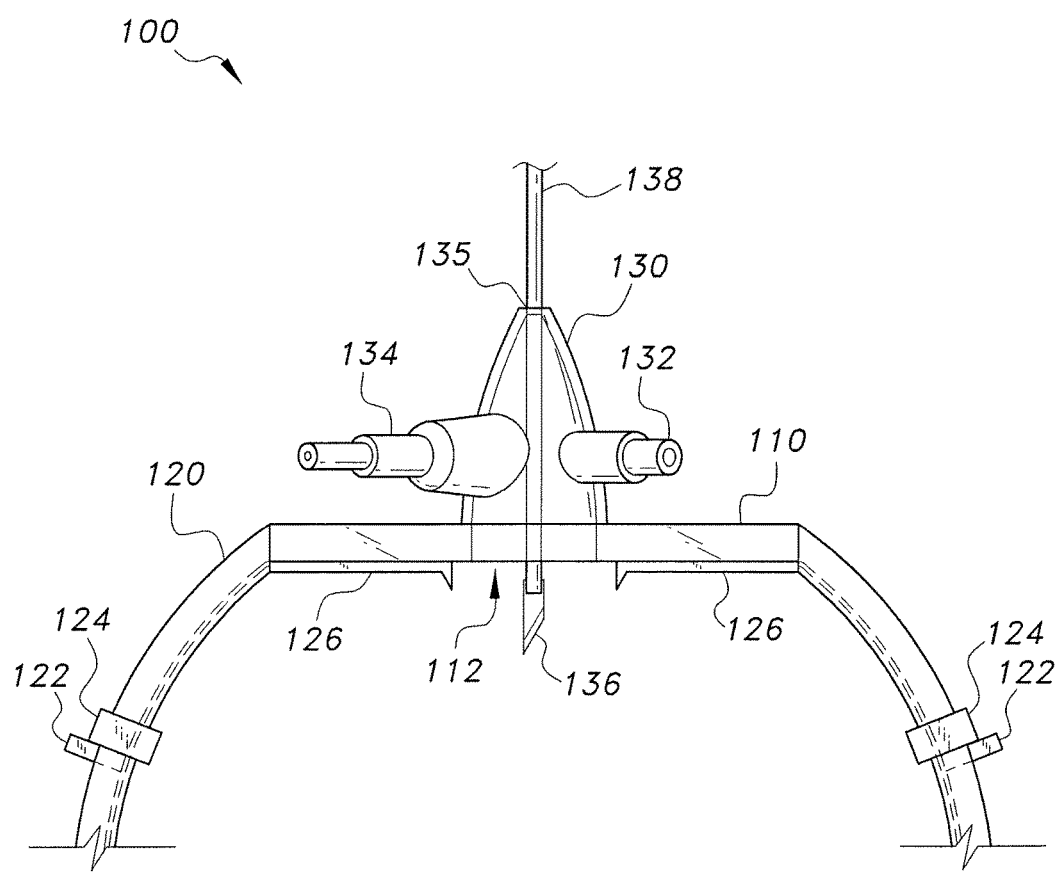
FIG. 3 is a partial side view of the device for sutureless repair of an injured nerve.

FIG. 3 shows a side view of the transparent membrane 110 and attached enclosure 130. The elongate member 138 is capable of translating along the upper opening 135 of the enclosure 130, allowing it to access the nerve during the procedure and to be retracted after the procedure. The lateral adjustability of the blade 126 is restricted by the size of the aperture 112 in the transparent membrane 110 and the height of the enclosure 130. The elongate member 138 has a pivot point at the aperture 135 though which it extends. Accordingly, the size of the opening 112 in the transparent membrane 110 may be increased and the enclosure 130 height may be decreased to increase the working area of the blade 136.

A method for using the device 100 begins with placing the transparent membrane 110 over an incision containing ends of a severed nerve, and wrapping the band 120 around the associated appendage. For example, if the severed nerve is on the forearm, the arm is inserted into the band 120, and the band 120 is adjusted so the transparent membrane 110 is over the incision.

When the severed nerve ends are exposed to air, they begin to die. Therefore, it is beneficial to attach the device 100 and begin the present process as quickly as possible. The transparent membrane 110 should be placed so the portion of the membrane between the approximation claws 126 completely surrounds the incision. This allows an air- and liquid-tight seal to be created between the transparent membrane 110 and the skin surrounding the incision. It is contemplated that multiple sizes of the device 100 may be made available for different sizes of incision.

Once the membrane 110 is sealed around the incision, a saline solution is pumped in through the inlet nozzle 132 and is concurrently allowed to drain out through the outlet nozzle 134. The flow of saline provides constant irrigation to the site, which removes all of the air from the sealed area below the membrane 110 to create a physiological healing environment. The irrigation also cleans the area by removing debris. Medication, such as growth factors and antibiotics, may be added to the saline.

Since the ends of the nerves were exposed to air, they will have begun to die. The practitioner will freshen up the nerve ends by using of the elongate member 138 and blade 136 to cut off the dead portions of the severed ends. Typically 1 mm is removed from each end. However, more may be removed if a portion larger than 1 mm is dead. The transparency of the membrane 110 allows the practitioner to perform the cutting while the nerve is in the sealed, air-free environment. The cut off portions of the nerves will be removed by the irrigation process.

Both of the freshened nerve ends will have only been exposed to the saline solution, and therefore will remain alive and be able to reattach. However, in order to reattach, the ends need to be approximated and aligned. The approximation claws 126 are adjusted by the practitioner, which, in turn, adjusts the tissue so that the nerve ends are approximated and aligned. The approximation claws 126 are adjusted by moving the adjustors 122. When the nerve ends are properly approximated, the keeper loops 124 lock the adjustor 122, and therefore the associated approximation claws 126, in place.

Once the nerve ends are aligned and approximated, the valve in the inlet nozzle 132 is closed, and a syringe is used to drain fluid out of the outlet nozzle 134 until the transparent membrane 110 collapses around the nerve. At this point the sealed area under the transparent membrane 110 is under a slight negative pressure. The slight negative pressure is maintained by shutting off the valve of the outlet nozzle 134 while the syringe is still attached to the outlet nozzle 134, thus preventing air from entering through the outlet nozzle 134. Once the transparent membrane 110 is collapsed around the nerve, the nerve ends are primarily held in place by the membrane 110, and the approximation claws 126 are no longer necessary. The negative pressure also assures that there is no air in the sealed area, which would negatively affect the nerve healing. In addition, the negative pressure may also promote neovascularization, which can positively affect healing.

Since two live nerve ends are approximated, they will reattach and act as a functioning nerve is a short period of time. The function of the nerve may be restored almost immediately, since a capillary affect will be produced through the channel created by the attached ends. Accordingly, there is no need for the proximal axon to grow though the channel of the dead distal axon, since Wallerian degeneration is avoided. The device is left in place for approximately one month, which allows the nerve to completely reattach under the air-free, saline condition. Once the nerve is fully healed, the device 100 can be removed and the incision closed.

Figure 4:
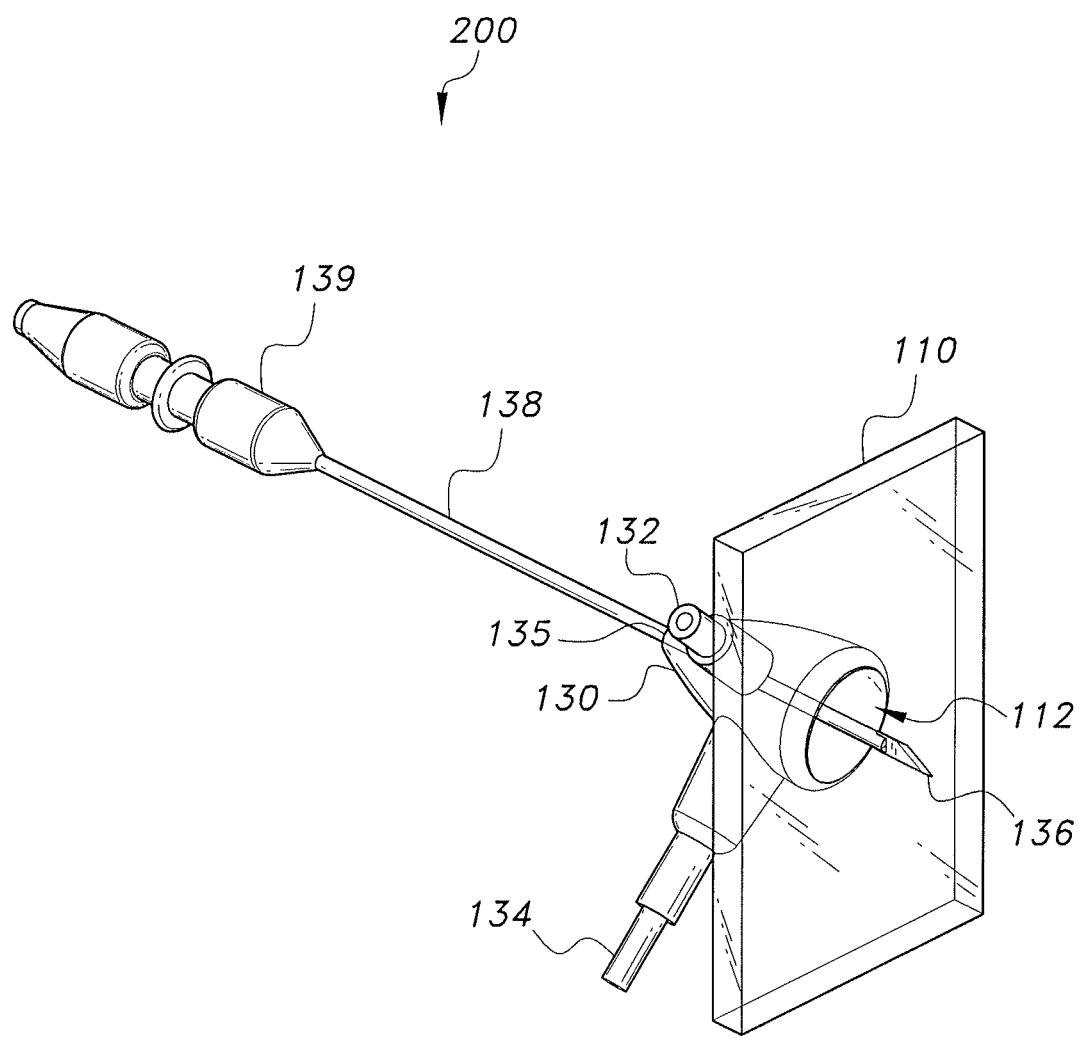
FIG. 4 is a perspective view of an alternative embodiment of the device for sutureless repair of an injured nerve.

The nerve repair procedure can be performed using an alternative device 200 without the band and approximation claws, as seen in FIG. 4. An assistant can be used to hold the transparent membrane 110 in place during the initial portion of the procedure, and also to approximate the nerves by manipulating the tissue upstream and downstream of the severed ends. Once the transparent membrane 110 is collapsed around the nerve ends, it will hold them in their approximated and aligned position. Accordingly, the procedure may be performed where the device 200 only includes the transparent membrane 110, the attached enclosure 130, and the blade 136 with attached elongate member 138, as seen in FIG. 4.

The device 100 or device 200 and associated method may be used with a nerve graft, for such situations as repairing a nerve defect. In these cases, a first device 100 or 200 will be placed at the proximal junction of the nerve graft and a second device 100 or 200 will be placed at the distal junction of the nerve graft.

It is to be understood that the device for sutureless repair of an injured nerve is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A device for sutureless repair of an injured nerve, comprising:
    a transparent membrane having an aperture defined therein, the membrane having opposing sides;
    a band attached to the opposing sides of the transparent membrane;
    an enclosure attached to the transparent membrane, the enclosure having an upper opening and a lower opening, the lower opening surrounding the aperture in the transparent membrane with an air-tight seal between the enclosure and the transparent membrane, the enclosure having an inlet nozzle and an outlet nozzle extending therefrom;
    an elongate member extending through the upper opening in the enclosure, the elongate member having a blade attached thereto extending below the membrane; and
    two approximation claws attached to the band on opposing sides of the transparent membrane.

2. The device for sutureless repair according to claim 1, further comprising adhesive disposed on a lower surface of the transparent membrane.

3. The device for sutureless repair according to claim 1, wherein the inlet nozzle includes a shutoff valve and the outlet nozzle includes a shutoff valve.

4. The device for sutureless repair according to claim 1, wherein the inlet nozzle includes a one-way valve permitting flow into the enclosure and the outlet nozzle includes a one-way valve permitting flow out of the enclosure.

5. The device for sutureless repair according to claim 1, wherein the inlet nozzle and the outlet nozzle create a flow path through the enclosure open to the aperture in the transparent membrane.

6. The device for sutureless repair according to claim 1, wherein the upper opening in the enclosure maintains an air-tight seal around the elongate member.

7. The device for sutureless repair according to claim 6, further comprising an O-ring disposed around the elongate member at the upper opening in the enclosure, the O-ring forming the air-tight seal between the upper opening and the elongate member.

8. The device for sutureless repair according to claim 1, wherein the band further includes two adjustors attached to the approximation claws, the adjustors being configured for adjusting the approximation claws relative to the band.

9. The device for sutureless repair according to claim 8, further comprising two keeper bands disposed on the band and configured to hold the adjustors in a set position.

10. The device for sutureless repair according to claim 1, wherein the elongate member is capable of pivoting, rotating, and translating relative to the enclosure.

11. The device for sutureless repair according to claim 1, further comprising a handle located at an end of the elongate member opposite the blade.

12. A nerve repair device for sutureless repair of an injured nerve comprising:
    a transparent membrane having opposing sides, an aperture defined therein, the membrane having an upper surface and a lower surface a band attached to the opposing sides of the transparent membrane;
    an enclosure attached to the upper surface of the transparent membrane, the enclosure having an upper opening and a lower opening, the lower opening surrounding the aperture in the transparent membrane with an air-tight seal between the enclosure and the transparent membrane, the enclosure further including an inlet nozzle and an outlet nozzle extending therefrom;
    an elongate member extending through the upper opening in the enclosure, the to elongate member having a blade attached thereto extending below the membrane; and
    adhesive disposed on the lower surface of the transparent membrane.

13. The device for sutureless repair according to claim 12, wherein the inlet nozzle includes a shutoff valve and the outlet nozzle includes a shutoff valve.

14. The device for sutureless repair according to claim 12, wherein the upper opening maintains an air-tight seal around the elongate member.

15. The device for sutureless repair according to claim 12, wherein the elongate member is capable of pivoting, rotating, and translating relative to the enclosure.

* * * * *